US007567871B2

United States Patent
Rohde et al.

(10) Patent No.: US 7,567,871 B2
(45) Date of Patent: Jul. 28, 2009

(54) AUTOMATIC MATERIAL LABELING DURING SPECTRAL IMAGE DATA ACQUISITION

(75) Inventors: David B. Rohde, Madison, WI (US); Patrick P. Camus, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 0 days.

(21) Appl. No.: 11/829,518

(22) Filed: Jul. 27, 2007

(65) Prior Publication Data

US 2008/0027657 A1 Jan. 31, 2008

Related U.S. Application Data

(60) Provisional application No. 60/820,537, filed on Jul. 27, 2006.

(51) Int. Cl.
*G01N 31/00* (2006.01)
*G01R 13/00* (2006.01)
(52) U.S. Cl. .............................. 702/28; 702/30; 702/66; 702/67
(58) Field of Classification Search .................... 702/28, 702/29, 194, 196, 30–32, 66–78, 189–193, 702/195, 197; 506/6; 356/401–403, 725
See application file for complete search history.

(56) References Cited

U.S. PATENT DOCUMENTS 6,584,413 B1 6/2003 Keenan et al.
6,675,106 B1 * 1/2004 Keenan et al. ................ 702/28

* cited by examiner

*Primary Examiner*—Eliseo Ramos Feliciano
*Assistant Examiner*—Phuong Huynh
(74) *Attorney, Agent, or Firm*—DeWitt Ross & Stevens; Michael C. Staggs

(57) ABSTRACT

A system for performing spectral microanalysis delivers analysis results during the course of data collection. As spectra are collected from pixels on a specimen, the system periodically analyzes the spectra to statistically derive underlying spectra representing proposed specimen components, wherein the derived spectra combine in varying proportions to result (at least approximately) in the measured spectra at each pixel. Those pixels having the same dominant proposed component, and/or which contain at least approximately the same proportions of the proposed components, may then have their measured spectra combined (i.e., added or averaged). These spectra may then be cross-referenced via reference libraries to identify the components actually present. During the foregoing analysis, the measured spectra are preferably condensed, as by reducing the number of energy channels/intervals making up the measured spectra and/or by combining the measured spectra of adjacent pixels, to reduce the size of the data cube and expedite analysis results.

11 Claims, 4 Drawing Sheets

AUTOMATIC MATERIAL LABELING DURING SPECTRAL IMAGE DATA ACQUISITION

CROSS-REFERENCE TO RELATED APPLICATIONS

This application claims priority under 35 USC §119(e) to U.S. Provisional Patent Application 60/820,537 filed 27 Jul. 2006, the entirety of which is incorporated by reference herein.

FIELD OF THE INVENTION

This document concerns an invention relating generally to spectral microanalysis (i.e., chemical microanalytical characterization of a specimen), and more specifically to methods for enhancing the speed of microanalysis.

BACKGROUND OF THE INVENTION

Scientists, technicians and other users often perform spectral microanalysis of specimens to determine the spatial composition of the specimen—in other words, what makes up the specimen (elements, compounds, alloys, phases, etc.) at various points about an area of interest on the specimen. In essence, spectral microanalysis yields a map of the specimen's composition, and can do so on a microscopic level, yielding an extremely useful tool for science and industry.

Spectral microanalysis is usually performed by directing an excitation beam—such as an electron beam or X-ray beam—at a specimen, and then capturing and analyzing the radiation and/or particles emitted by the specimen in response to the excitation beam. Often, data related to the emitted radiation and/or particles are presented to a user as a spectral histogram (or simply a "spectrum"), wherein the counts (numbers) of emissions from the specimen are plotted versus their energy. Most distinct substances generate a unique spectrum, and thus the substance's spectrum serves as a "fingerprint" for the substance. By capturing spectra from a specimen and then cross-referencing these spectra versus catalogues/databases of "reference spectra"—spectra captured from known substances—one can determine the substances present in the specimen. Usefully, the aforementioned spectra can often be collected along with an image of the specimen, thereby allowing an analyst a useful visual reference against which the spectral (substance identification) data may be reviewed. Thus, one can both view the analyzed region of interest on the specimen, and also determine the composition of the specimen at the viewed region.

Several factors tend to complicate microanalysis. Initially, since specimens rarely consist of pure substances, one usually cannot simply identify the "closest" reference spectrum and assume that it identifies the substance. Rather, a spectrum captured from a specimen often reflects the presence of several substances, each being present in different amounts within the specimen. Thus, the specimen spectrum equates to a combination of the spectra of the component substances, with each component spectrum having a strength within the combination which corresponds to the relative amount of that component. As a result, analyzing a spectrum captured from a specimen to determine its component spectra (and this its component substances) often requires complicated and time-consuming statistical methods.

Further, the method described above only provides information about (i.e., a spectrum for) the area of the specimen which is subjected to the excitation beam. Thus, if one wishes to obtain information about a larger region of the specimen, the excitation beam must be scanned across the specimen (e.g., in an X-Y "rastering" pattern), and spectra must be collected at multiple points during the scan. This leads to large amounts of data, and consequently large data analysis times.

To better illustrate these difficulties, it is useful to consider common spectral microanalysis methods in greater detail. As an excitation beam is scanned between areas or "pixels" distributed about a specimen, a spectrum is collected at each pixel. Each spectrum contains information regarding the elements present in the specimen at the pixel from which the spectrum was captured. In addition, data resulting from the excitation beam is also captured at each pixel and can be used to generate an image of the pixel. For example, where the excitation beam is an electron beam, the image may depict the pixel's backscattered electrons (electrons from the excitation beam which were "reflected" from the specimen), or the pixel's secondary electrons (electrons knocked out of the specimen by the excitation beam). In either case, the image provides a visual representation of the pixel, though the visual representation may not correspond to the pixel's appearance if viewed by the eye under standard light; for example, a backscattered electron image effectively provides a view of the pixel's density, and a secondary electron image effectively provides a view of the pixel's surface roughness. The combination of the spectrum and image data at a particular pixel is often referred to as a "hyperspectral image," or as a "hyperspectral data cube" when referring to the spectra and image data over the entire scanned region (i.e., over all pixels).

The spectra from the various pixels are then statistically analyzed via Principal Component Analysis (PCA) to determine which components (i.e., compounds or other combinations of elements) seem most likely to be present in the scanned region of the specimen, and at each pixel in the scanned region. In PCA methods, the correlations between the pixel spectra are determined to extract the spectra of the underlying components that seem to be present in the various pixels across the scanned region. This results in a set of statistically-derived spectra, each representing a component, wherein these derived spectra of all of these (derived) components combine in varying proportions at each of the pixels to result in the measured spectra at the pixels.

The information regarding the derived components and their proportions can then be extended to the measured hyperspectral images to determine their likely components. For example, one could look to each pixel and determine the dominant component at that pixel (i.e., the derived component which seems present in greatest amounts at that pixel, and/or which seems to be most likely to be present at that pixel), and then combine/average the measured spectra of all pixels having that same dominant component. The combined spectrum—which at least theoretically represents the component(s) present at its respective pixels—can then be assigned to each of the pixels having that same dominant component. This step, which replaces the measured spectrum for each pixel with its corresponding combined spectrum, can result in a smaller and more manageable set of spectra for the pixels. These spectra can then each be processed versus databases of reference spectra to determine the probable real-world components at each pixel. If desired, the image(s) of the specimen can then have the name(s) of the calculated components overlaid over the areas to which they correspond, or the image can be color-coded or otherwise encoded/labeled to allow a user to visualize the composition of the specimen.

The aforementioned statistical analysis of the measured pixel spectra is often performed by a commercially available software package known as COMPASS, details of which are described in greater detail in U.S. Pat. Nos. 6,584,413 and 6,675,106. While COMPASS is a valuable microanalysis tool, it suffers from the drawback that it can be time-consuming to use: since there are many pixels (e.g., over a million pixels across a 1024×1024 pixel area), and the correlations between their unique measured spectra must be calculated to determine their probable components (and these spectra may themselves consist of thousands of data points, e.g., counts measured across 4096 energy intervals or "bins"), it can require many minutes to provide the desired output, even where exceptionally fast computer processing speeds are used. Other analysis packages, which may employ different statistical processing methods than those of the aforementioned patents, tend to incur similar processing times. This is disadvantageous because an analyst naturally wants microanalysis results as soon as possible.

SUMMARY OF THE INVENTION

The invention involves methods for performing spectral microanalysis and statistical analyses of microanalysis data cubes, as well as devices and systems for performing such methods, wherein the invention is intended to at least partially address the aforementioned problems. To give the reader a basic understanding of some of the advantageous features of the invention, following is a brief summary of preferred versions of the methods, with reference being made to the accompanying drawings to enhance the reader's understanding. Since this is merely a summary, it should be understood that more details regarding the preferred versions may be found in the Detailed Description set forth elsewhere in this document. The claims set forth at the end of this document then define the various versions of the invention in which exclusive rights are secured.

Initially, spectra are collected from a set of pixels spaced about a region of interest on the specimen. This is preferably done by repeated scanning of the excitation beam over the region of interest on the specimen, with spectra being collected from the pixels during each scan. This is schematically depicted in the accompanying FIG. 1 at step A, wherein an emitter 100 is shown directing an excitation beam at a specimen 10 so that radiation and/or particles emitted by a pixel 12 (i.e., the location of impingement by the excitation beam) can be detected by a detector 102. Here, sixteen pixels are depicted (though usually a scanned region of interest would have far more, e.g., a 1024×1024 array of pixels rather than a 4×4 array), and the emitter 100 might scan the pixels row-by-row and then repeat the scan so that two or more spectra are collected for each pixel during the course of the scans. The spectra collected from the pixels 12 are shown below the specimen 10 in the form of histograms including emission counts (i.e., counts of emissions from the pixel in response to the incident excitation beam) which are sorted into a series of discrete energy intervals, with all counts within an interval having corresponding energies fitting within the interval. With each successive scan, all spectra collected for each respective pixel can be combined (e.g., added or averaged), thereby generating a combined spectrum for each pixel. This combination process beneficially results in a spectrum with enhanced signal-to-noise ratio because noise present in a pixel's successive individual spectra tends to "average out" in its combined spectrum.

Analysis of the spectra, and output of the probable components present at the pixels, are then preferably performed during collection of the spectra rather than thereafter (as in COMPASS and other prior microanalysis methods). As a result, an analyst can be provided with preliminary microanalysis results while collection of spectra is still underway. Such results may be rough or incomplete, but they may nevertheless allow an analyst to begin drawing conclusions regarding a specimen, to plan further experimentation, or to take other steps which rely on microanalysis results to proceed. As previously noted, conventional analysis is computationally burdensome and time-consuming, and thus it is somewhat impractical to perform conventional analysis during the course of data collection (at least with use of computer processing speeds which are commonly available at the time this document was prepared). Thus, one or more of the following steps is recommended to reduce analysis time and burden, and to hasten output.

First, the size of the data (e.g., the hyperspectral data cube) can be significantly reduced by "condensing" the spectra collected from the pixels: by combining the emission counts in adjacent energy intervals within each spectrum, as schematically illustrated in FIG. 1 at step B. As an example, it is conventional to collect spectra which each have counts measured across 4096 channels, with each channel spanning a 10 eV energy interval. Such spectra could be condensed to 2048 channel spectra, each having channels 20 eV wide (as exemplified by step B as shown in FIG. 1, wherein the emission counts in each set of two adjacent channels/intervals are combined); to 1024 channel spectra, each having channels 40 eV wide; or to 512 channel spectra, each having channels 80 eV wide. It has been found that condensing a spectrum by a factor of n results in an increase in analysis speed of approximately n squared (e.g., reducing the number of channels or "bins" by ½ increases analysis speed by a factor of approximately 4). Thus, the invention could (for example) perform a first scan over the specimen's region of interest to collect a first set of pixel spectra, and could then process these spectra (and deliver output) in parallel with a subsequent scan to collect a second set of pixel spectra. The analysis of the first set can be greatly expedited by condensing the spectra in the aforementioned manner, and the probable components determined by the analysis can be delivered to the analyst as data collection proceeds.

It is notable that condensing spectra to fewer channels/intervals will inherently decrease their resolution, and it might be expected that this would have a significant adverse impact on analysis: since the probable components present within the spectra are statistically determined by looking at their correlations, and extracting the common constituents therefrom, it would seem that reducing the number of channels/intervals would generate false or inaccurate correlations and lead to erroneous identification of components. Surprisingly, this has not been found to be the case, at least when the number of channels are condensed to a lesser extent (e.g., halved or quartered). In any event, the primary fault arising from condensing the spectra tends to be that one or more components—generally those that are present in the specimen in lesser amounts—go unidentified, rather than having components be misidentified. Additionally, as data collection progresses and the analyst is presented with at least some preliminary microanalysis results, the degree to which the spectra are condensed may be reduced so that the resolution of the output might be enhanced. For example, after a first scan, the channels of the spectra might be reduced by a factor of four, and the analyst might be rapidly provided with preliminary output identifying the probable components present at the pixels (perhaps along with a warning that the output is merely approximate at this point). When the second scan is complete, the channels of the spectra might be reduced by a factor of two, and the analyst can then be provided with updated output identifying the probable specimen components. These results may simply verify the prior output, or they may exhibit more accurate component identification at certain pixels. After the third or some subsequent scan, analysis might proceed without condensing the spectra, thereby providing the analyst with even higher accuracy in component identification. By following this approach, the analyst is rapidly provided with at least approximate microanalysis results, and these are subsequently periodically updated to enhance their resolution.

A second useful method of decreasing analysis time is to spatially condense the pixels, i.e., to combine the spectra in adjacent pixels, as schematically illustrated in FIG. 1 at step C. As an example, a 1024×1024 pixel matrix can be condensed to a 512×512 matrix by averaging or adding the spectra of adjacent sets of 2×2 pixels, a 256×256 matrix by averaging or adding the spectra of adjacent sets of 4×4 pixels, etc. In step C as illustrated in FIG. 1, the spectra of each set of 4 adjacent pixels are combined, thereby condensing the 16 spectra shown in step A to the 4 spectra shown in step C. As with condensing the energies of the spectra, condensing the pixels also serves to reduce the size of the data cube and decrease analysis times, and the accuracy of the analysis does not significantly degrade (at least when only immediately adjacent pixels are combined, e.g., when a 1024×1024 is condensed to a 512×512 matrix). Also similarly to condensing spectral energies, the degree to which the pixels are condensed may be varied during the course of data collection, e.g., larger numbers of pixels may be condensed during early stages of data collection so that component output can be more rapidly provided to an analyst, and as data collection progresses and the analyst has obtained at least preliminary output, the degree of condensation may be reduced, or pixels need not be condensed at all.

Thus, spectral and/or spatial condensation may be applied to allow more rapid analysis, and the analysis can occur in parallel with further data collection so that the analyst need not await results from the collection and analysis of an entire standard data cube. To illustrate, where both condensation methods are applied, the processing time required for statistical analysis is generally reduced from several minutes to only a few seconds (by use of computer processors in common use at the time this document was prepared). Alternatively, where processor capacity is limited, data collection might periodically be halted so that analysis and output of data can occur, with the analyst being presented with interim analysis results before data collection resumes. In either case, the analyst's productivity is effectively increased because the analyst is able to begin drawing conclusions and making decisions at an earlier stage than in prior microanalysis methods.

The analysis of the (preferably condensed) spectra, depicted at step D of FIG. 1, can be performed by the multivariate statistical methods described in the aforementioned U.S. Pat. Nos. 6,584,413 and 6,675,106, or by any other suitable methods. Preferably, the correlations between the spectra are calculated to generate a set of proposed component spectra, wherein the proposed component spectra combine in varying proportions at each pixel to at least approximately result in the spectra actually collected from the pixels. Pixels having similar proposed component content may then be combined (e.g., their spectra may be averaged or added, as depicted at step E), and these combined spectra may be cross-referenced versus one or more libraries of reference spectra to determine the components which are probably present at the pixels (as depicted at step F). As a simple example, those pixels which are determined to be dominated by (i.e., to predominantly contain) a particular proposed component may have their spectra combined and cross-referenced versus reference libraries to assign probable components to these pixels. Alternatively or additionally, those pixels which have similar proportions of the same components (e.g., all pixels having 30-35% of proposed component A, 30-35% of proposed component B, and 30-35% of proposed component C) may have their spectra combined and cross-referenced versus reference libraries to assign probable components to these pixels.

Once the probable components are assigned to the pixels, they may be output to an analyst in a variety of forms (as shown at step G of FIG. 1). Preferably, the output includes at least three components: an image of the region of interest (or at least a portion thereof), e.g., a backscattered or secondary electron image (preferably with color-coding, or other encoding, applied to indicate the presence of different probable components); labels naming the probable components of at least some of the pixels within the region of interest (as by simply providing a list of the names of the probable components as they are identified in the reference libraries, perhaps with the percentage of each probable component within the region of interest); and the spectrum for each of the probable components. Preferably, the analyst also has the ability to move a cursor or other pointer over any pixel within the displayed image of the region of interest to display the collected spectrum for that pixel, as well as other information (e.g., the probable components present at that pixel, their percentages, etc.).

Further advantages, features, and objects of the invention will be apparent from the remainder of this document in conjunction with the associated drawings.

BRIEF DESCRIPTION OF THE DRAWINGS

FIGS. 3A-3C illustrate exemplary output that might be obtained from the invention after 10 seconds of data collection and analysis of the region of interest of FIG. 2, wherein FIG. 3A illustrates probability maps wherein the density (darkness) or a pixel/region depicts the probability that one of three probable components is present at that pixel, FIG. 3B depicts corresponding binary maps wherein a darkened pixel indicates that a certain probable component is dominant (most probable) at that pixel (and conversely a white pixel indicates that a certain probable component is unlikely at that pixel), and FIG. 3C illustrates the reference spectra obtained when the pixels of each of FIGS. 3A-3C each have their respective spectra combined and cross-referenced versus a reference library of spectra.

DETAILED DESCRIPTION OF THE PREFERRED VERSIONS OF THE INVENTION

To expand on the foregoing Summary, FIGS. 2-5 show output that might be obtained from an exemplary version of the invention. An analyst can load a desired specimen into a spectrometer of the desired form, e.g., a spectrometer for energy-dispersive X-ray spectrometry (EDS), FT-IR and/or Raman spectrometry, electron energy-loss spectrometry (EELS), secondary ion mass spectrometry (SIMS), auger electron spectrometry, or any other spectrometer which collects specimen characteristics (such as mass, energy or wavenumber emissions) on a pixel-by-pixel basis. The analyst might then input desired measurement settings, such as the location and size of the region of interest (e.g., 256×256 pixels, 1024×1024 pixels, etc.), the "frame" or "exposure" time over which emissions are to be captured from each pixel, the number of times the set of pixels is to be scanned, and so forth. Once data collection begins, the collected data can periodically be analyzed to provide output to the analyst as data collection proceeds. For example, after each scan over the region of interest, or after some time interval (e.g., 10 seconds) has expired, the system might analyze the data that has thus far been collected and provide output to the analyst so that the analyst might begin formulating conclusions and future actions while data acquisition proceeds. Any conclusions based on preliminary data analysis results can be revised as data collection proceeds, and as updated or final analysis results are made available to the analyst.

Figure 1:
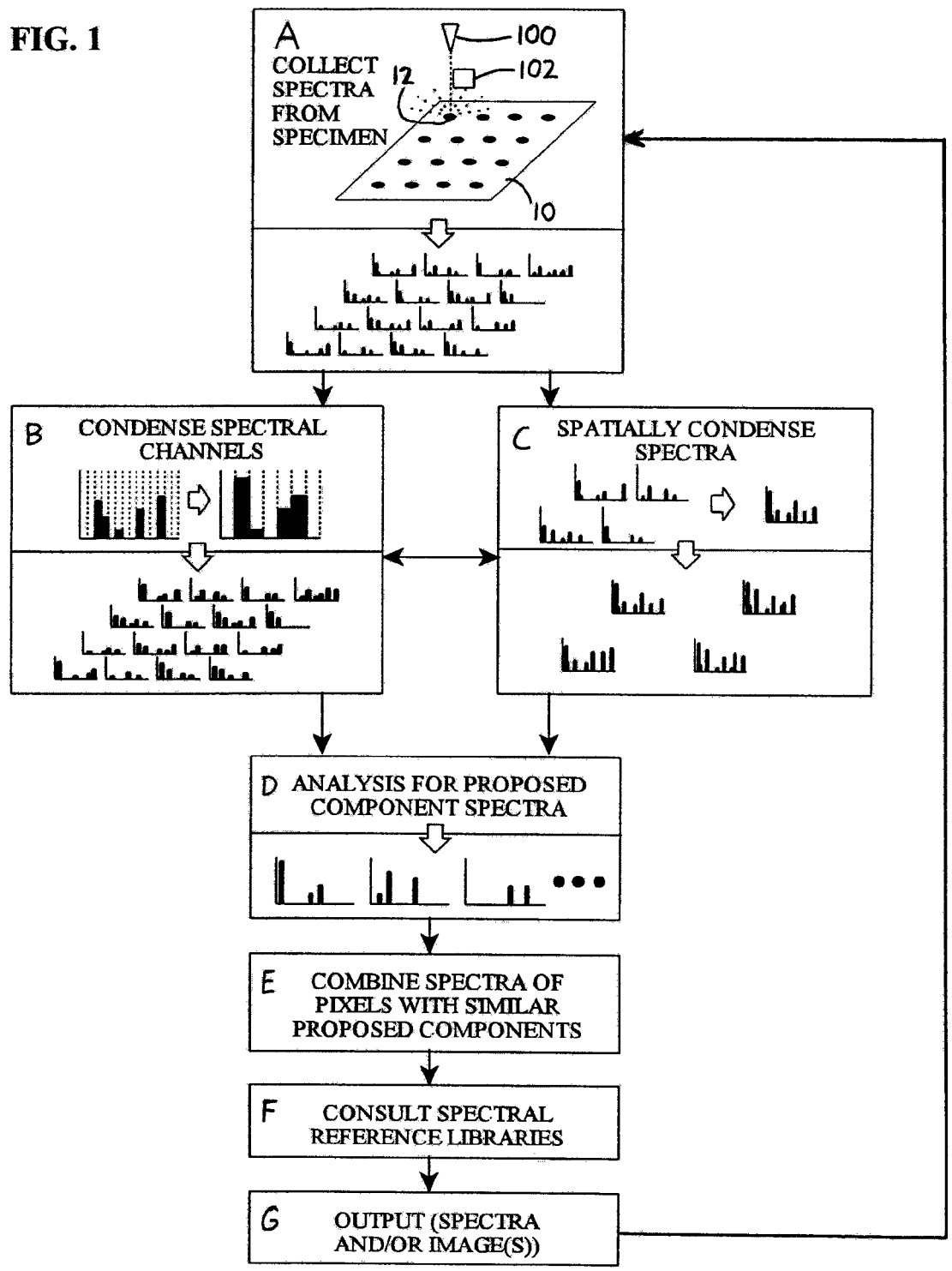
FIG. 1 is a flowchart schematically presenting a preferred form of the invention, wherein a region of interest 10 on a specimen is scanned to collect spectra from a set of pixels 12 (step A); the spectra are then condensed by combining the emission counts in adjacent energy intervals (channels) within the spectra (step B), and/or by combining the spectra of adjacent pixels (step C); the condensed spectra are then analyzed to identify probable components present at the pixels (step D); the spectra of the pixels having similar probable components (and proportions thereof) are then combined (step E); the resulting spectra are cross-referenced via reference spectra to determine their actual components (step F); and the results are then output to the analyst (step G).
Figure 2:
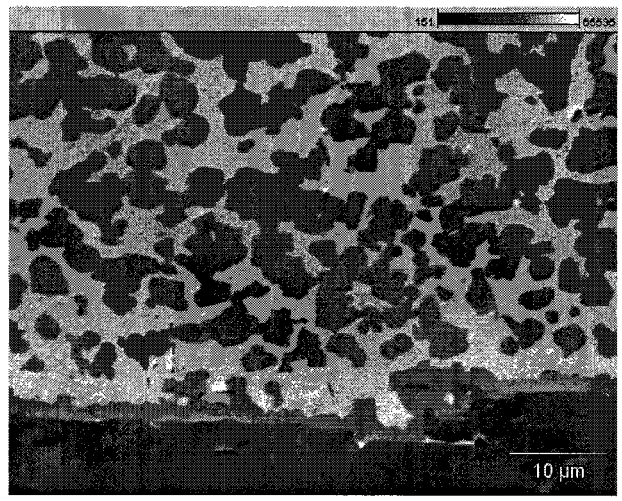
FIG. 2 is an image (e.g., an electron image) of a region of interest on a specimen.
Figure 3A:
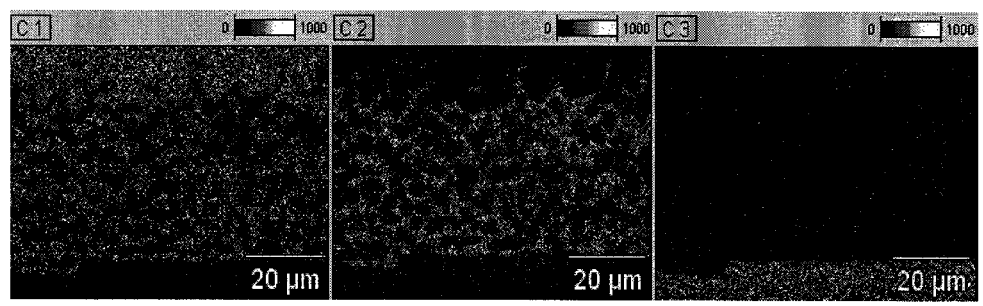
Figure 3B:
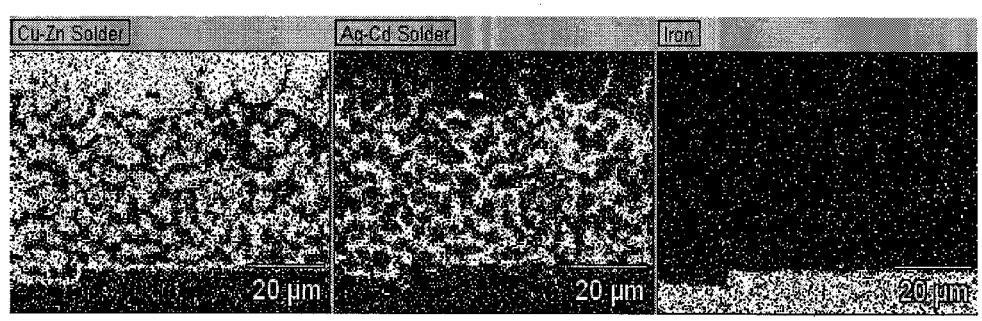
Figure 3C:
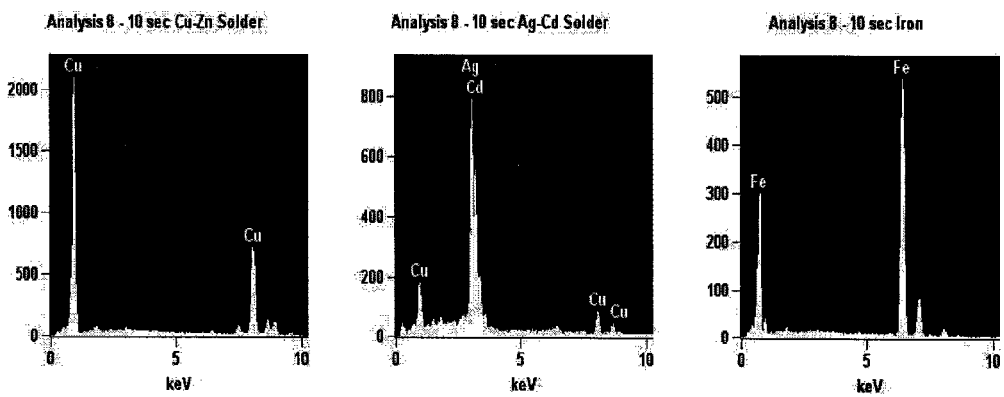

To illustrate this process in greater depth, FIGS. 3A-3C illustrate exemplary results from the specimen of FIG. 2 after data have been collected for 10 seconds (as in step A in FIG. 1), condensed (steps B and/or C in FIG. 1), and analyzed and output (steps D-G in FIG. 1). The step of condensing the collected spectra—i.e., "energy binning" (combining adjacent energy intervals/channels) and/or "spatially binning" (combining the spectra of adjacent pixels) the spectra—is optional, but unless the data cube is reduced by these or similar steps, it is difficult to process the collected data with sufficient speed that meaningful analysis results can be supplied during the course of data collection. As discussed previously, during analysis, the spectra of the various pixels are analyzed for their correlation to determine some set of proposed component spectra, wherein the proposed component spectra appear to combine in varying proportions to result in the measured spectra at the various pixels. In FIGS. 3A-3C, three proposed components—Cu—Zn (copper-zinc solder), Ag—Cd (silver-cadmium solder), and Fe (iron)—appear probable based on the data cube collected thus far, and FIG. 3A illustrates calculated probability maps wherein the pixel density (pixel darkness) represents the probability that a specified one of the probable components is present at a given pixel. FIG. 3B then depicts maps corresponding to those of FIG. 3A, but wherein probabilities are presented in binary form, with a dark pixel indicating that a certain probable component is dominant (most probable) at that pixel, and conversely a white pixel indicating that a certain probable component is unlikely at that pixel. The spectra of FIG. 3C are then obtained if the measured spectra corresponding to each of the component pixels—i.e., the dark pixels for each of the Cu—Zn, Ag—Cd, and Fe binary maps of FIG. 3B—are combined, and then cross-referenced versus libraries of reference spectra.

Figure 4A:
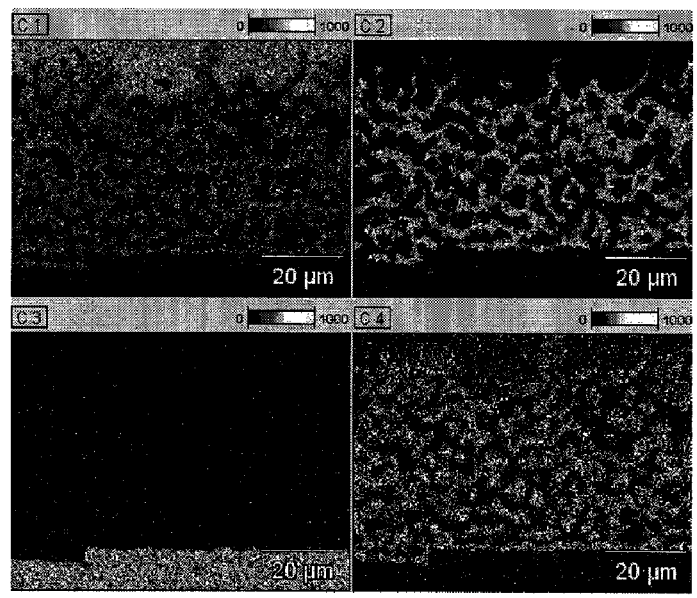
FIGS. 4A-4C illustrate exemplary output that might be obtained from the invention after 30 seconds of data collection and analysis of the region of interest of FIG. 2, with an additional component (Cu in addition to Fe, Cu—Zn, and Ag—Cd) being identified here owing to the larger data cube (with 30 seconds of data rather than merely 10).
Figure 4B:
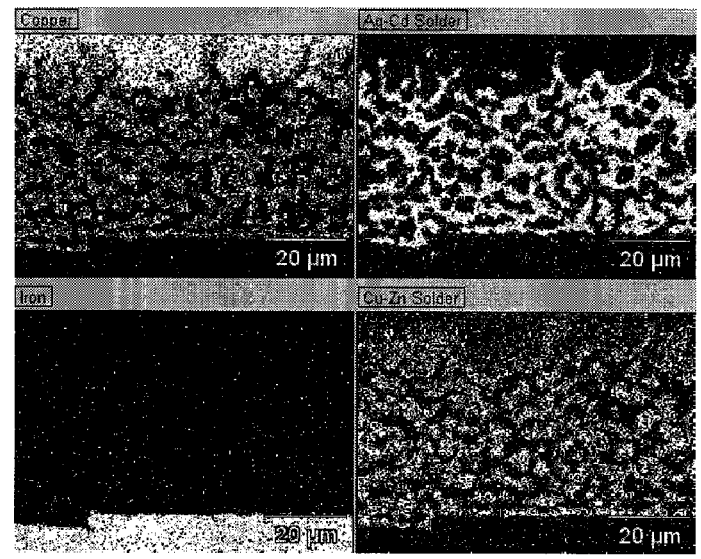
Figure 4C:
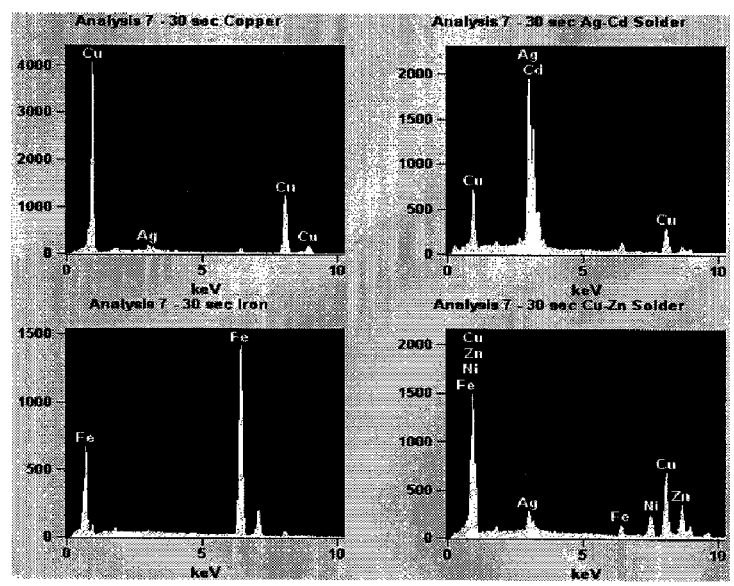

FIGS. 4A-4C then show corresponding proposed components, probability maps, and spectra after 30 seconds of data collection. At this point, the data cube is larger, and sufficient spectra are present which indicate a the presence of a distinct fourth probable component (Cu) that this component now appears present in the specimen.

Figure 5:
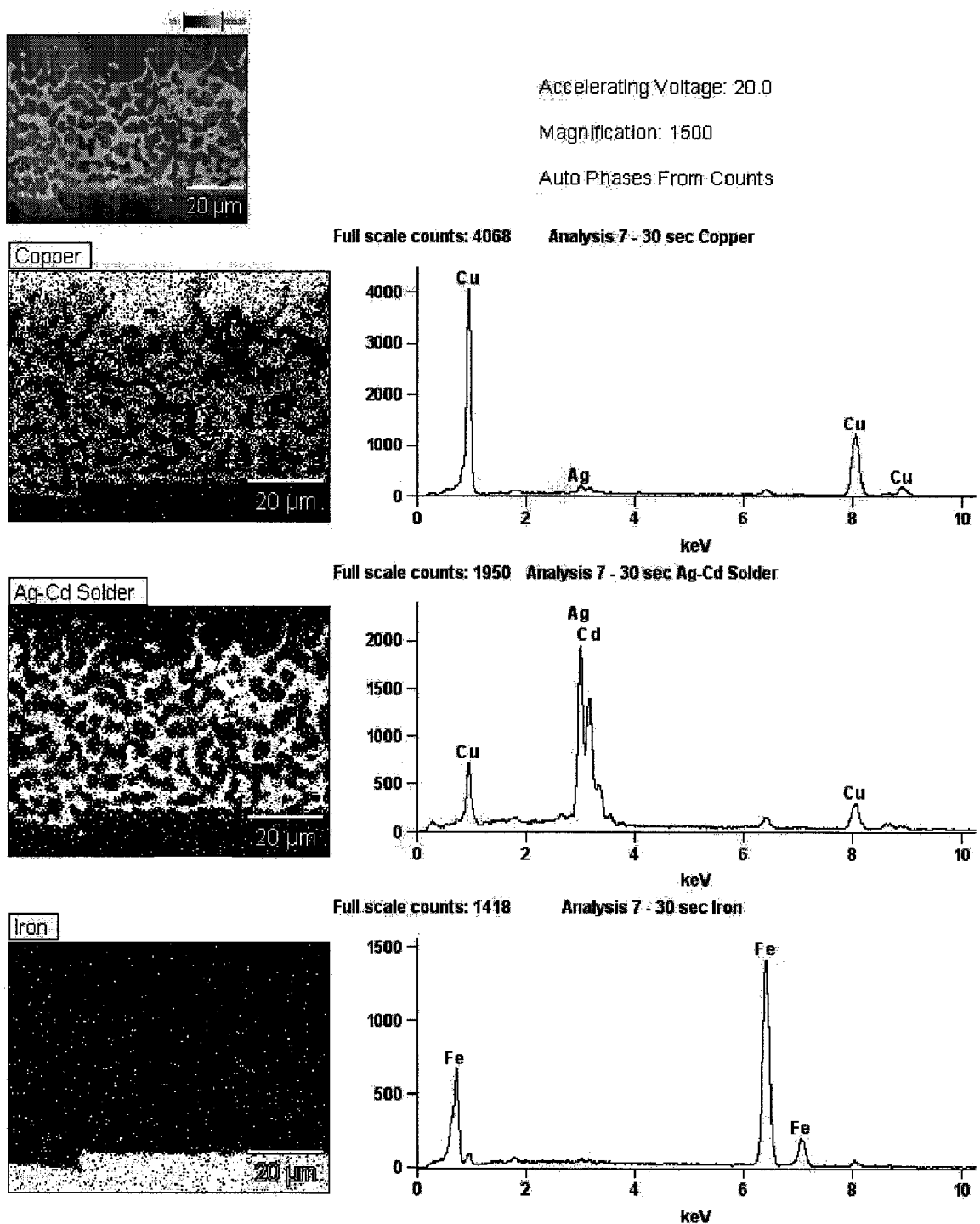
FIG. 5 illustrates an exemplary final report that might be generated and presented to an analyst after data collection is completed on the region of interest of FIG. 2 (e.g., after 60 seconds of data collection), with an image of the region of interest being presented along with corresponding binary images showing where each predicted component is dominant, and also with the reference spectra obtained when the pixels corresponding to each of the dominant components each have their respective spectra combined and cross-referenced versus a reference library of spectra.

FIG. 5 then presents a view of a report that might be presented to an analyst, with the report here showing the image of the specimen, the binary probability maps for each probable component (which effectively amount to maps of where each probable component is the dominant component in the specimen), and the corresponding reference spectra. This report might be presented to the analyst after all data collection is complete, and/or it could be presented at some earlier time (e.g., after some period or time or number of data collection scans).

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A method for performing spectral microanalysis of a specimen, the method including the steps of:
    a. collecting spectra from pixels spaced about a region of interest on the specimen, wherein each spectrum includes emission counts measured across a range of energies;
    b. periodically during the collection:
        (1) condensing the collected spectra, wherein the condensing of the collected spectra comprises at least one step selected from: combining the emission counts in adjacent energy intervals within the range of energies and spatially combining the spectra in adjacent pixels;
        (2) analyzing the condensed spectra while collecting the spectra thus far to determine the probable components present at the pixels, and
        (3) outputting the probable components present at the pixels includes displaying: a. an image of at least some of the pixels within the region of interest, and b. labels naming the probable components of at least some of the pixels within the region of interest.

2. The method of claim 1 wherein the number of adjacent energy intervals whose emission counts are combined is varied as collection progresses.

3. The method of claim 1 wherein the number of adjacent energy intervals whose emission counts are combined is reduced as collection progresses.

4. The method of claim 1 wherein the step of outputting the probable components present at the pixels further includes displaying the spectra of one or more of the pixels within the region of interest.

5. The method of claim 1 wherein the step of outputting the probable components present at the pixels includes displaying, for any user-selected pixel:
   a. the spectrum collected at the user-selected pixel, and
   b. one or more of the probable components present at the user-selected pixel.

6. The method of claim 1 wherein the step of outputting the probable components present at the pixels further includes displaying the spectra of one or more of the probable components of at least some of the pixels within the region of interest.

7. The method of claim 1 wherein the step of collecting spectra from pixels spaced about a region of interest includes:
   a. scanning the area of interest at least twice, and
   b. collecting spectra from the pixels during each scan, whereby two or more spectra are collected for each pixel.

8. The method of claim 7 wherein, after the second and subsequent scans, the collected spectra for each respective pixel are combined.

9. The method of claim 1 wherein the step of analyzing the spectra collected thus far to determine the probable components present at the pixels includes the steps of:
   a. calculating a set of proposed component spectra, wherein the proposed component spectra combine in varying proportions at each pixel to at least approximately result in the spectra collected from the pixels;
   b. combining the spectra of the pixels having the same proposed component spectrum present as the maximum proportion of their proposed component spectra;
   c. cross-referencing the combined spectra versus one or more libraries of reference spectra to determine the components present at the pixels.

10. The method of claim 1 wherein the step of analyzing the spectra collected thus far to determine the probable components present at the pixels includes the steps of:
    a. calculating a set of proposed component spectra, wherein the proposed component spectra combine in varying proportions at each pixel to at least approximately result in the spectra collected from the pixels;
    b. combining the spectra of the pixels wherein the proposed component spectra combine in at least substantially the same proportions;
    c. cross-referencing the combined spectra versus one or more libraries of reference spectra to determine the components present at the pixels.

11. A method for performing spectral microanalysis of a specimen, the method including the steps of:
    a. repeatedly scanning a region of interest on the specimen, wherein
       (1) during each scan, spectra are collected from a set of pixels spaced about the region of interest, and
       (2) the collected spectrum from each pixel includes emission counts, wherein the emission counts are sorted into discrete energy intervals;
    b. before completion of all scans of the region of interest:
       (1) for each pixel:
          (a) combining all spectra thus far collected, thereby generating a combined spectrum; and
          (b) condensing the combined spectrum, wherein the condensing of the combined spectrum comprises at least one step selected from: combining the emission counts in adjacent energy intervals within the range of energies and spatially combining the spectra in adjacent pixels thereby generating a condensed spectrum;
       (2) analyzing the condensed spectrum for the pixels to identify probable components present at the pixels, and
       (3) displaying:
          (a) an image, and
          (b) labels naming the probable components,
          of at least some of the pixels.

\* \* \* \* \*